(12) United States Patent
Hijikata et al.

(10) Patent No.: US 6,423,037 B1
(45) Date of Patent: Jul. 23, 2002

(54) REDUCED-PRESSURE SYRINGE AND MANUFACTURING METHOD THEREFOR

(75) Inventors: Shigeki Hijikata; Nobuyuki Natori; Norio Watanabe, all of Fujieda; Kouichi Sugita, Osaka, all of (JP)

(73) Assignee: Kaken Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/555,252

(22) PCT Filed: Nov. 27, 1998

(86) PCT No.: PCT/JP98/05338

§ 371 (c)(1),
(2), (4) Date: May 26, 2000

(87) PCT Pub. No.: WO99/27982

PCT Pub. Date: Jun. 10, 1999

(30) Foreign Application Priority Data

Dec. 1, 1997 (JP) .............................................. 9-330014

(51) Int. Cl.[7] .................................................. A61M 5/00
(52) U.S. Cl. ........................ 604/232; 604/235; 604/187
(58) Field of Search ................................ 604/181, 182, 604/187, 200, 201, 202, 218, 221, 232, 235, 244

(56) References Cited

U.S. PATENT DOCUMENTS

| | | | |
|---|---|---|---|
| 3,901,402 A | * 8/1975 | Ayres | 215/248 |
| 4,599,082 A | * 7/1986 | Grimard | 604/90 |
| 4,613,326 A | * 9/1986 | Szwarc | 604/89 |
| 4,952,208 A | * 8/1990 | Lix | 604/187 |
| 5,184,450 A | 2/1993 | Galy et al. | |
| 5,489,266 A | * 2/1996 | Grimard | 604/89 |
| 5,637,100 A | 6/1997 | Sudo | |
| 5,685,846 A | * 11/1997 | Michaels, Jr. | 604/90 |
| 5,752,940 A | * 5/1998 | Grimard | 604/181 |
| 5,899,881 A | * 5/1999 | Grimard et al. | 604/89 |

FOREIGN PATENT DOCUMENTS

| | | |
|---|---|---|
| EP | 0 664 136 A2 | 7/1995 |
| JP | 7-75672 A | 3/1995 |
| JP | 7-213608 A | 8/1995 |
| JP | 7-213609 A | 8/1995 |
| JP | 8-112333 A | 5/1996 |

* cited by examiner

*Primary Examiner*—Gregory Huson
*Assistant Examiner*—Huyen Le
(74) *Attorney, Agent, or Firm*—Merchant & Gould P.C.

(57) ABSTRACT

A-syringe for storing a freeze-dried agent therein under reduced pressure as well as a method for manufacturing the syringe. A specified amount of a chemical is injected into a cartridge with the one end of the cartridge down. The gasket is plugged halfway on the other end side of the cartridge, so that the cartridge is made communicating between inside and outside by the recessed groove, in which state the chemical is freeze-dried. The sealing cap is overlaid on an upper end face of the gasket and the sealing cap is pushed in the reduced-pressure atmosphere so that the other end side of the cartridge is sealed by the gasket and the sealing cap. The sealing cap is engaged with an end face of the cartridge on the other end side, thereby being prevented from moving into the cartridge.

3 Claims, 8 Drawing Sheets

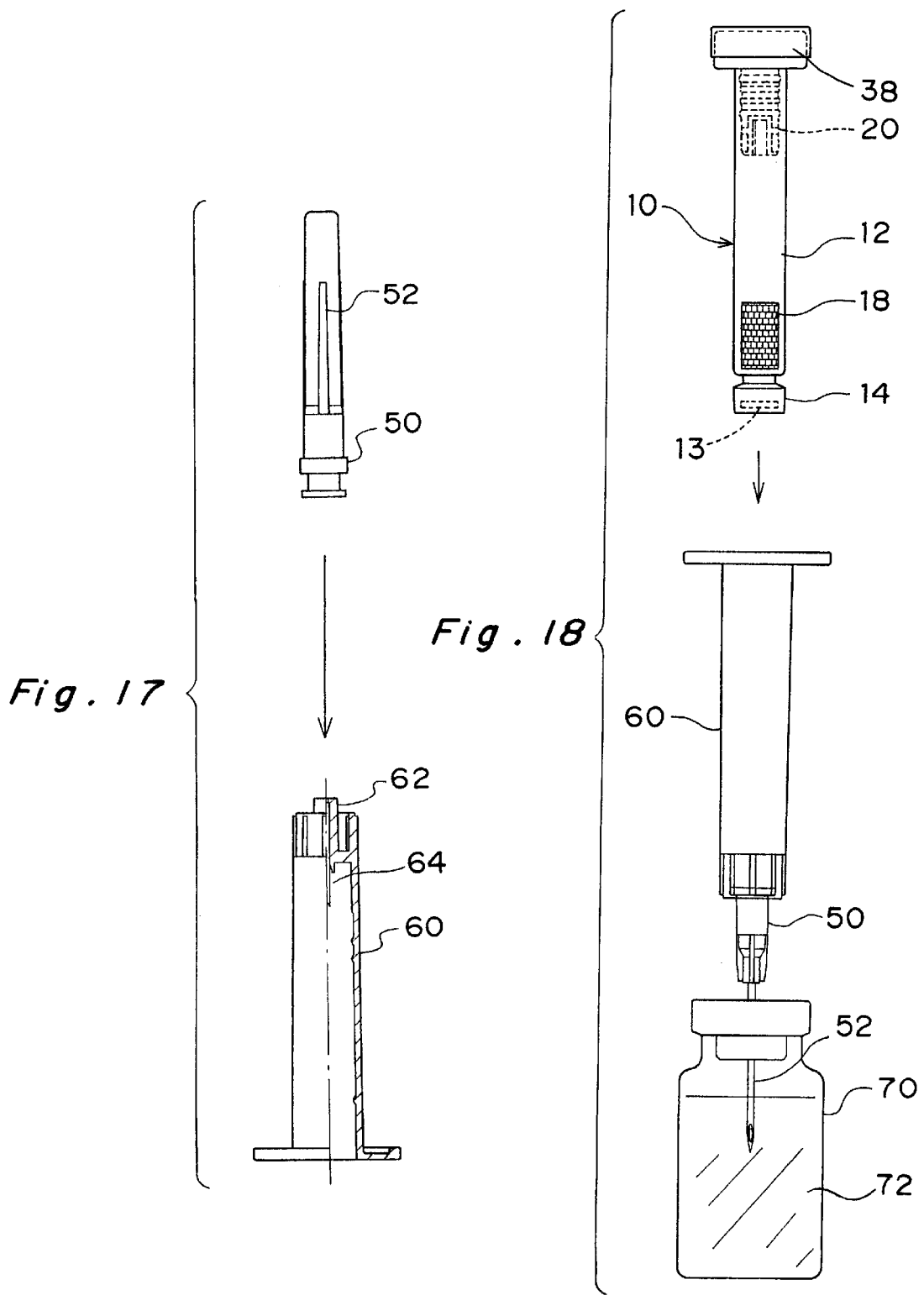

US 6,423,037 B1

REDUCED-PRESSURE SYRINGE AND MANUFACTURING METHOD THEREFOR

TECHNICAL FIELD

The present invention relates to a reduced-pressure syringe and its manufacturing method. More particularly, the invention relates to a reduced-pressure syringe for storing a freeze-dried agent therein under reduced pressure as well as a method for manufacturing the reduced-pressure syringe.

BACKGROUND ART

Conventionally, among freeze-dried agents, which are dissolved before use, some are unstable and prone to be decomposed with moisture, oxygen and the like, while others have a tendency that foams will not disappear at the dissolution. Such freeze-dried agents, including antibiotics, growth hormones and vaccines, are generally stored in a vial under reduced pressure, lower than atmospheric pressure, with a view to stable storage and prevention of foaming at dissolution. However, in one case where a chemical is stored in a vial, the chemical needs to be moved to a syringe after dissolved, not ready for instant use. In another case where a chemical resulting from dissolution of a freeze-dried agent has a high viscosity, the chemical is difficult to suck up. For these and other reasons, it is considered convenient to provide a prefilled syringe in which a freeze-dried agent is stored under reduced pressure.

Unfortunately, however, it has been impossible for conventional prefilled syringes to store a freeze-dried agent under reduced pressure.

More specifically, for sealing a freeze-dried agent into a syringe, generally, for example as shown in FIG. 1, a chemical 2 is injected into a cartridge 1 with its one sealed end down, and the cartridge 1 is plugged halfway on the other end side with a gasket 3. Then, while the cartridge 1 is held communicating between inside and outside through slit grooves 4 formed in the outer circumferential surface of lower part of the gasket 3, the chemical 2 is freeze-dried in a freeze dryer. That is, the chemical 2 is frozen and reduced in pressure so that its moisture is removed, by which a freeze-dried agent 2' is formed.

Next, as shown in FIG. 2, with the reduced-pressure state held, the gasket 3 is pushed all the way into the syringe 1 by a shelf 5 of the freeze dryer so that the freeze-dried agent 2' is sealed and accommodated in the syringe 1. Thereafter, as shown in FIG. 3, the syringe 1 is taken out from the freeze dryer and a cap 6 for packaging use is attached to the other end of the syringe 1. The syringe, when taken out from the reduced-pressure freeze dryer into atmospheric pressure, undergoes a pressure difference from atmospheric pressure due to the fact that interior of the gasket 3, i.e., interior of the cartridge 1 is in a reduced-pressure state. Therefore, the gasket 3 is further pushed into the syringe 1 by atmospheric pressure. As a result, the space in which the freeze-dried agent 2' is sealed and accommodated goes smaller into a generally atmospheric-pressure state, thus making it impossible to store the freeze-dried agent 2' under reduced pressure (for example, Japanese Patent Laid-Open Publication HEI 7-213608).

DISCLOSURE OF THE INVENTION

Accordingly, a technical object of the present invention is to provide a reduced-pressure syringe, as well as a manufacturing method therefor, for storing a freeze-dried agent under reduced pressure.

In order to achieve the above technical object, the present invention provides a reduced-pressure syringe having the following constitution.

The reduced-pressure syringe of the present invention is basically so structured that within a generally cylindrical-shaped cartridge having a pair of ends in which one of the ends is openably sealed, a gasket having a pair of end faces is slidably provided on a side of the other of the ends of the cartridge, thereby defining a sealed space, where a freeze-dried agent is accommodated in the sealed space, and in which the gasket has, in its outer circumferential surface, a recessed groove continuing from one of the end faces of the gasket on the side of the one of the ends of the cartridge toward the other of the end faces thereof on the side of the other of the ends thereof to an intermediate position therebetween. The syringe further comprises sealing cap which is to be engaged with an end face of the cartridge on the side of the other of the ends and which seals the side of the other threreof. A pressure in the sealed space is held lower than atmospheric pressure.

Preferably, the reduced-pressure syringe having the above constitution is manufactured by the following method.

That is, the syringe comprises: a generally cylindrical-shaped cartridge having a pairs of ends in which one of the ends is openably sealed; a gasket having a pair of end faces and having, in its outer circumferential surface, a recessed groove continuing from one of the end faces of the gasket toward the other of the end faces thereof to an intermediate position therebetween; and a sealing cap. The method for manufacturing the reduced-presseure syringe comprises first, second and third steps. In the first step, a specified amount of a chemical in injected into the cartridge with the one of the ends of the cartridge. In the second step, the gasket is inserted halfway on a side of the other of the ends of the cartridge, into which the chemical has been ted, with the recessed groove of the gasket down, so that the cartridge is made communicating between inside and outside through the recessed groove, and then the chemical placed within the cartridge is freeze-dried in a freeze-drying chamber under a reduced-pressure atmosphere. In the third step, the sealing cap is overlaid on upper one of the end faces of the gasket and pushing the sealing cap toward the cartridge side in the freeze-drying chamber under the reduced-pressure atmosphere so that the side of the other of the ends of the cartridge is sealed by the gasket and the sealing cap, and that the sealing cap is engaged with an end face of the cartridge on the side of the other of the ends thereof.

In this manufacturing method, by the second step, a freeze-dried agent is formed on the lower side, i.e. the side of the one of the ends, of the cartridge. By the third step, the gasket is pushed into the cartridge, so that the cartridge is sealed on both sides thereof, i.e. on the side of the one of the ends of the cartridge where the freeze-dried agent is formed (i.e., sealed space) and on the side of the other of the ends of the cartridge where the gasket and sealing cap are placed, respectively, under a pressure lower than atmospheric pressure. While the syringe is kept in the freeze-drying chamber, freeze-drying process and plugging process of the gasket and the sealing cap can be carried out continuously under a reduced-pressure atmosphere. Preferably, the freeze-drying and plugging processes are carried out with the sealing cap overlaid on the upper end face of the gasket.

The reduced-pressure syringe having the above constitution is sealed with its interior in a reduced-pressure state, for example, by the above manufacturing method. Even if this syringe is taken out from the freeze-drying chamber having a reduced-pressure atmosphere into atmospheric pressure, the sealing cap is never pushed into the cartridge of the reduced-pressure state by atmospheric pressure because the sealing cap is engaged with the end face of the cartridge on the side of the other of the ends so as to be inhibited from moving into the syringe. Thus, the sealed space, in which the freeze-dried agent is accommodated, is held in the reduced-pressure state. Furthermore, if a space is present between the sealing cap and the gasket, the space is also held in the reduced-pressure state.

Therefore, the freeze-dried agent can be stored in the syringe under reduced pressure.

Preferably, the gasket has a fitting hole for fitting a plunger rod to the other of the end faces of the gasket on the side of the other of the ends of the cartridge. The sealing cap has a positioning protrusion which is to be inserted into the fitting hole of the gasket, the positioning protrusion being provided in an end face of the sealing cap on the side of the one of the ends of the cartridge.

With this arrangement, by inserting the positioning protrusion of the sealing cap into the fitting hole of the gasket, the sealing cap can be overlaid and positioned on the end face of the gasket on the side of the other of the ends of the cartridge and this state can be held. Thus, the work of plugging the sealing cap with the sealing cap overlaid on the gasket and, at the same time, pushing the gasket into the cartridge becomes easily attainable.

BRIEF DESCRIPTION OF THE DRAWINGS

FIGS. 17 to 21 are explanatory views of how to use the reduced-pressure syringe of FIG. 4.

BEST MODE FOR CARRYING OUT THE INVENTION

Hereinafter, a reduced-pressure syringe 10 according to an embodiment of the invention as shown in FIGS. 4 to 21 is described in detail.

Figure 1:
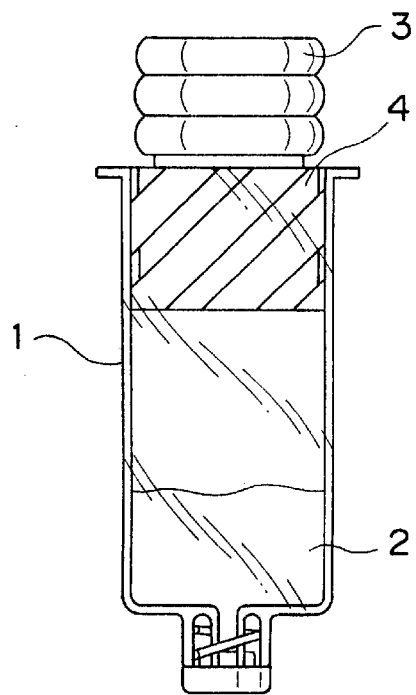
FIGS. 1, 2 and 3 are explanatory views of a syringe according to the prior art.
Figure 2:
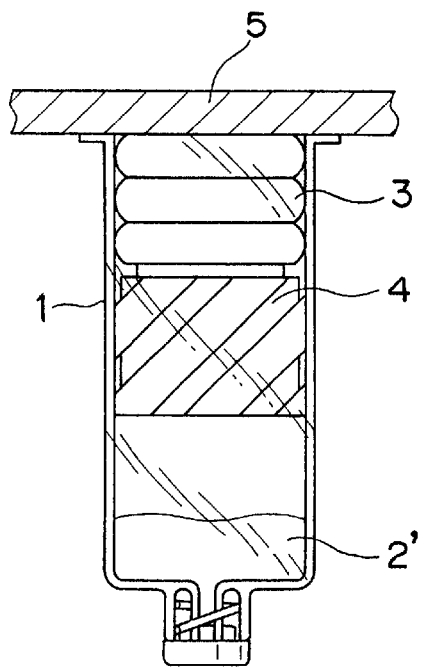
Figure 3:
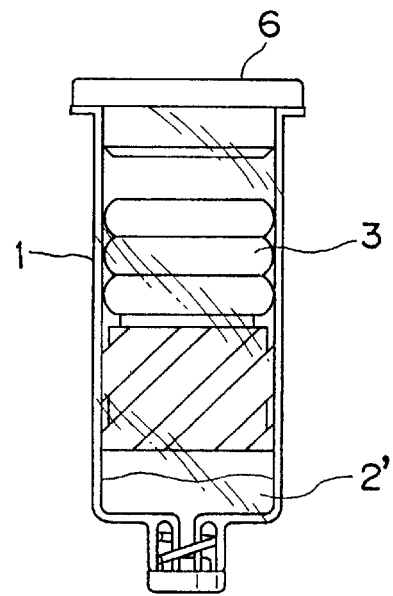
Figure 4:
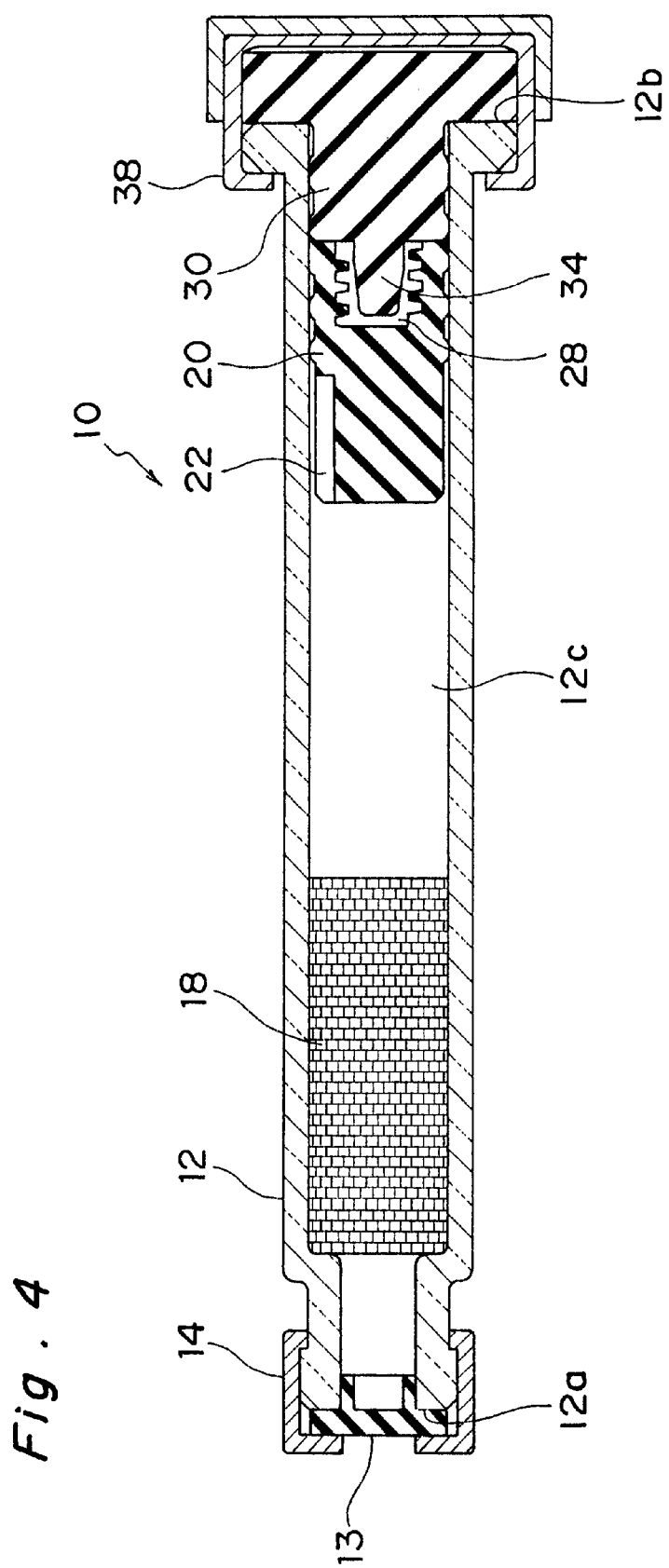
FIG. 4 is a sectional view of a reduced-pressure syringe according to an embodiment of the present invention.

The reduced-pressure syringe 10, as shown in the sectional view of FIG. 4, roughly comprises a cartridge 12, a gasket 20 and a sealing cap 30, where a freeze-dried agent 18 is sealed within a sealed space 12c defined in the cartridge 12 under a pressure lower than atmospheric pressure.

The cartridge 12 has a tubular main body. At one end 12a of the cartridge 12, a rubber packing 13 is fixed and sealed by an aluminum cap 14. At the other end 12b of the cartridge 12, a flange is provided so as to extend radially outwardly.

Figure 5:
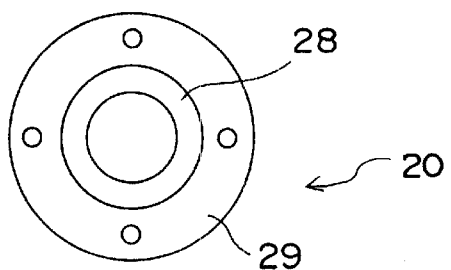
FIG. 5 is a plan view of the gasket in the reduced-pressure syringe of FIG. 4.
Figure 6:
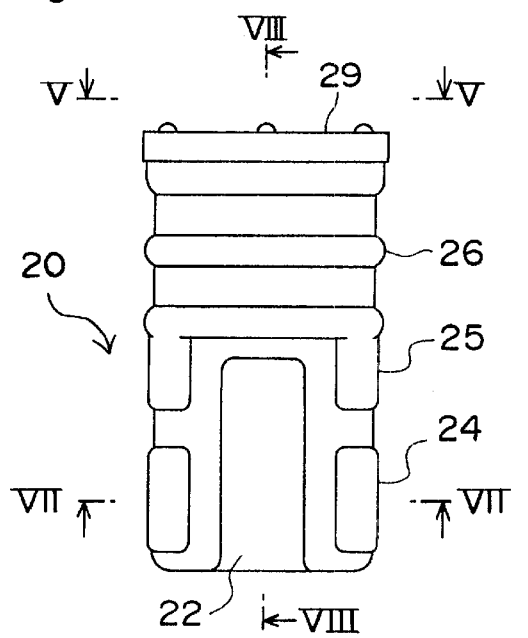
FIG. 6 is a front view of the gasket in the reduced-pressure syringe of FIG. 4.
Figure 8:
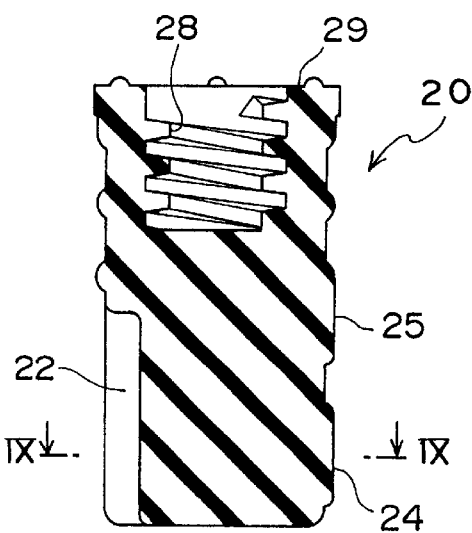
FIG. 8 is a longitudinal sectional view of the gasket in the reduced-pressure syringe of FIG. 4.
Figure 7:
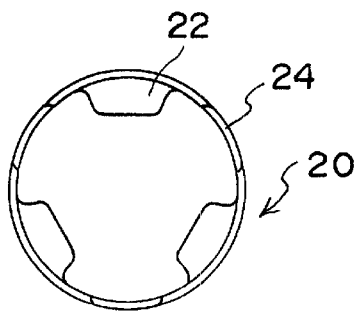
FIG. 7 is a bottom view of the gasket in the reduced-pressure syringe of FIG. 4.
Figure 9:
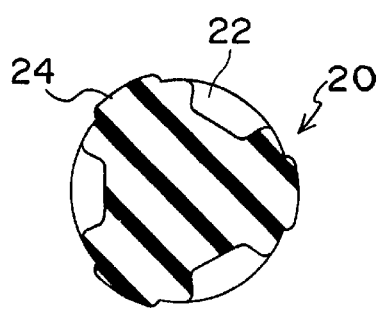
FIG. 9 is a cross sectional view of the gasket in the reduced-pressure syringe of FIG. 4.

The gasket 20, as detailed in FIGS. 5 to 9, is formed into a generally cylindrical shape. FIG. 5 is a plan view, FIG. 6 is a front view, FIG. 7 is a bottom view, FIG. 8 is a longitudinal sectional view and FIG. 9 is a cross sectional view. As shown in the drawings, in the outer circumferential surface of lower part of the cylindrical main body, recessed grooves 22 are formed so as to continue upward from the lower end side to an intermediate position. In the outer circumferential surface of lower part of the gasket 20, first and second temporary-stopper protrusions 24, 25 are swollen out so as to extend axially along the recessed grooves 22. The first and second temporary-stopper protrusions 24, 25 are placed so as to be axially spaced from each other, making it readily detectable that the gasket 20 is inserted halfway on the other end 12b side of the cartridge 12. In the outer circumferential surface of upper part of the gasket 20, annular sealing protrusions 26 are swollen out. The outer diameter of each protrusion 26 is slightly larger than the inner diameter of the inner circumferential surface of the cartridge 12. A screw hole 28 is formed in the upper surface 29 of the gasket 20 so that a plunger rod 40 can be screwed thereinto as described later.

Figure 10:
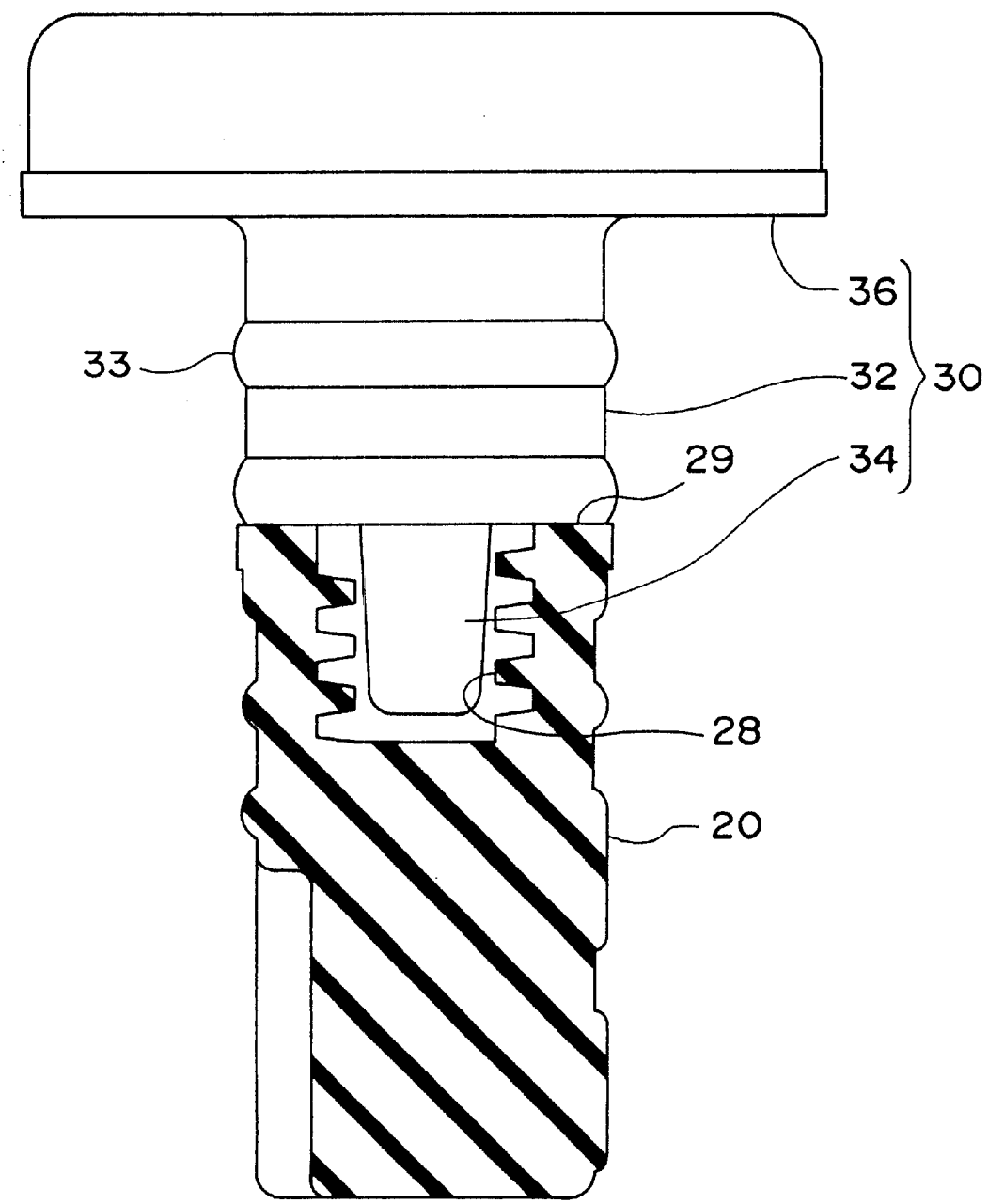
FIG. 10 is a plan view of the sealing cap of FIG. 4, also showing a section of the gasket.

The sealing cap 30, as detailed in the front view of FIG. 10, roughly comprises a cylindrical main body 32, a positioning protrusion 34 and a flange 36. In the outer circumferential surface of the main body 32, annular sealing protrusions 33 are swollen out. The outer diameter of the annular sealing protrusions 33 is slightly larger than the inner diameter of the inner circumferential surface of the cartridge 12. The positioning protrusion 34 protrudes downward from the lower surface of the main body 32. The sealing cap 30 can be overlaid on the upper surface 29 of the gasket 20 shown in its section in FIG. 10, and the positioning protrusion 34 can be inserted into the screw hole 28 of the gasket 20 and held generally coaxial with the gasket 20. The flange 36 extends radially outwardly from the top of the main body 32. The outer diameter of the flange 36 is generally equal to the outer diameter of the flange provided at the other end 12b of the cartridge 12.

The freeze-dried agent 18 is sealed and accommodated in the cartridge 12 through the procedure shown in the explanatory view of FIGS. 11 to 16.

Figure 11:
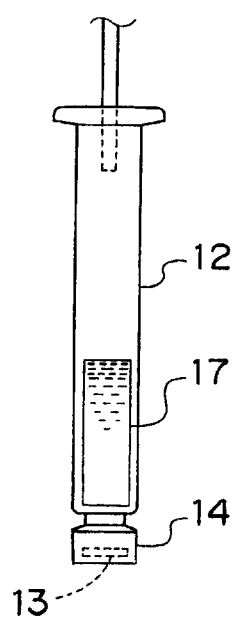
FIGS. 11 to 16 are explanatory views of manufacturing process for the reduced-pressure syringe of FIG. 4.

More specifically, as shown in FIG. 11, one end 12a of the cartridge 12 sealed by the rubber packing 13 and the aluminum cap 14 is positioned down, in which state a specified amount of a chemical 17 is injected into the cartridge 12.

Figure 12:
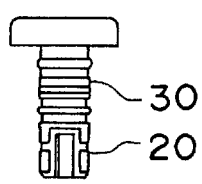

Next, as shown in FIG. 12, the sealing cap 30 is overlaid on the gasket 20, and the gasket 20 and the sealing cap 30 are held generally coaxial with each other by the positioning protrusion 34 and the screw hole 28 as described before.

Figure 13:
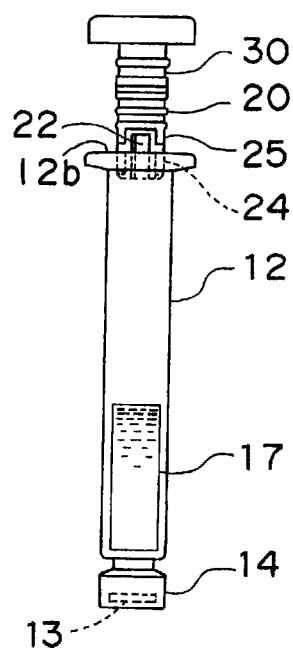

Next, as shown in FIG. 13, while held coaxial with the sealing cap 30, the gasket 20 is inserted halfway on the other end 12b side of the cartridge 12, that is, until the other end 12b of the cartridge 12 is positioned between the first and second temporary-stopper protrusions 24 and 25 of the gasket 20. In this state, the recessed grooves 22 of the gasket 20 are positioned with their top portions upper than the other end 12b of the cartridge 12, thus making the cartridge 12 communicating between inside and outside.

Figure 14:
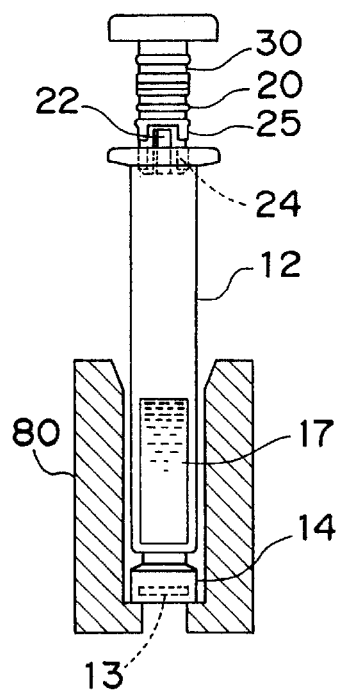

Next, the chemical 17 in the cartridge 12 is freeze-dried by using a freeze dryer. More specifically, as shown in FIG. 14, in the semi-plugged state that the cartridge 12 is communicating between inside and outside through the recessed grooves 22 of the gasket 20, the cartridge 12 is supported by an erecting jig 80 and placed on a shelf in the unshown freeze dryer. Then, the chemical 17 is frozen in the freeze dryer and thereafter moisture and the like are removed by reducing the internal pressure of the dryer. The moisture and the like of the frozen chemical 17 escape out of the cartridge 12 through the recessed grooves 22 of the gasket 20, by which a freeze-dried agent 18 is formed.

Figure 15:
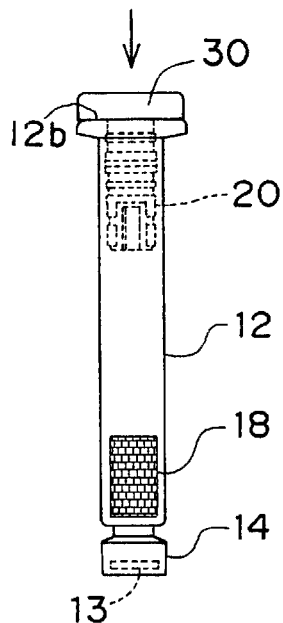

Next, with the reduced-pressure state held, as shown in FIG. 15, the sealing cap 30 is pushed into the syringe 12 with the shelf of the unshown freeze dryer until the flange 36 of the sealing cap 30 is engaged with the flange on the other end 12b side of the cartridge 12, so that the other end 12b side of the syringe 12 is sealed by the sealing protrusions 26 of the gasket 20 and the sealing protrusions 33 of the sealing cap 30. As a result, the freeze-dried agent 18 is sealed and accommodated in the cartridge 12 under reduced pressure.

Figure 16:
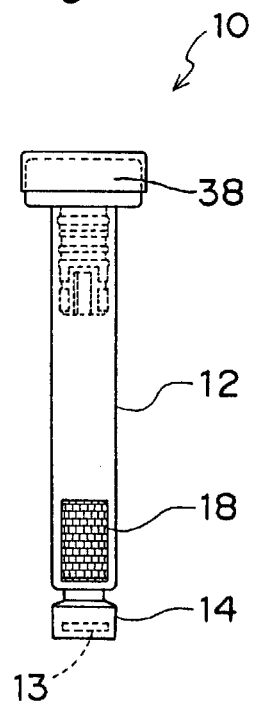

Thereafter, the cartridge 12 with both ends 12a, 12b sealed is taken out from the freeze dryer and, as shown in FIG. 16, the other end 12b side of the cartridge 12 is tightly wound up with a removable flip-off type aluminum cap 38. Thus, the reduced-pressure syringe 10 is completed.

When the cartridge 12 with both ends 12a, 12b sealed is taken out from within the reduced-pressure freeze dryer into atmospheric pressure, the outside atmospheric pressure acts on the sealing cap 30. However, because the outside flange 36 of the sealing cap 30 is engaged with the other end 12b side flange of the cartridge 12, the sealing cap 30 holds in its position, as it is, without being further pushed into the cartridge 12 by atmospheric pressure. The gasket 20, which is located further inside the cartridge 12 than the sealing cap 30, holds in its position, as it is, unless the sealing cap 30 changes in position, so that the sealed space 12c, in which the freeze-dried agent 18 is accommodated, is held under reduced pressure.

Figure 21:
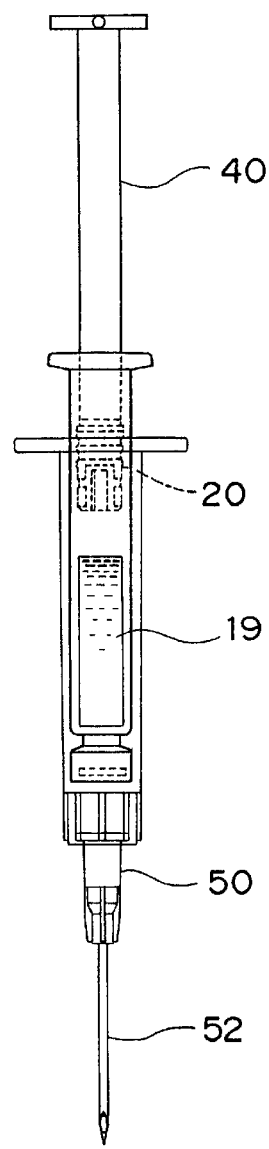

Next, an example of how to use the reduced-pressure syringe 10 is explained with reference to FIGS. 17 and 21.

Figure 19:
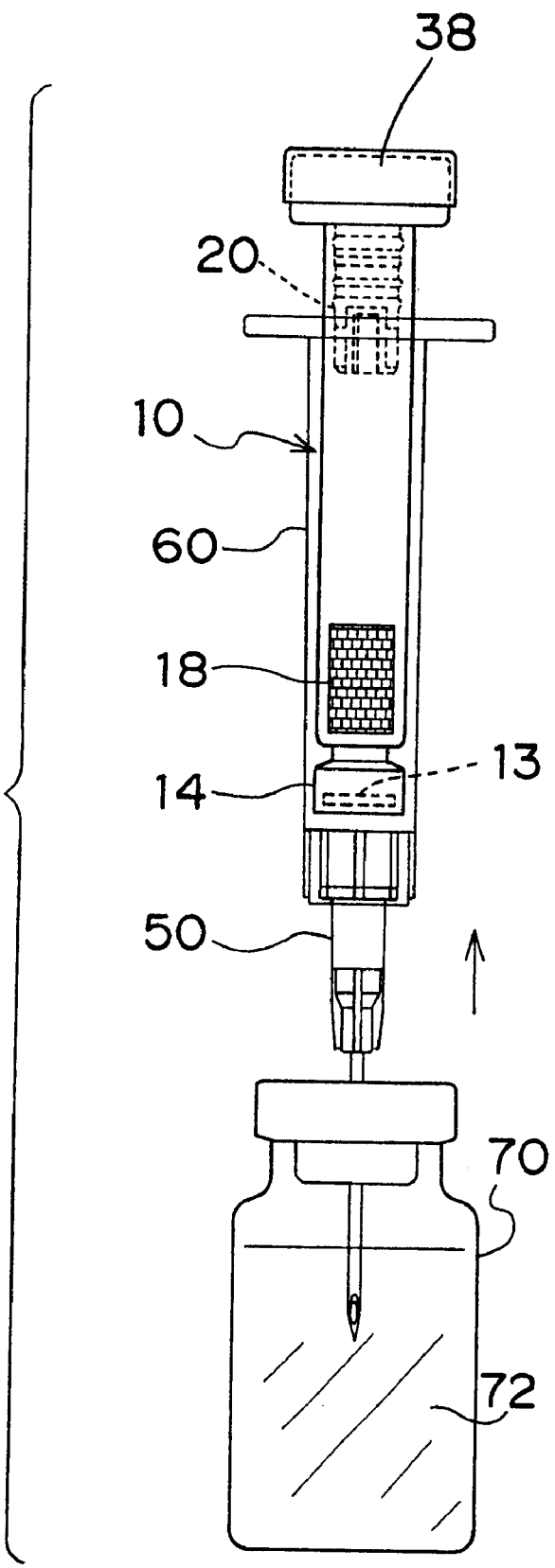
Figure 20:
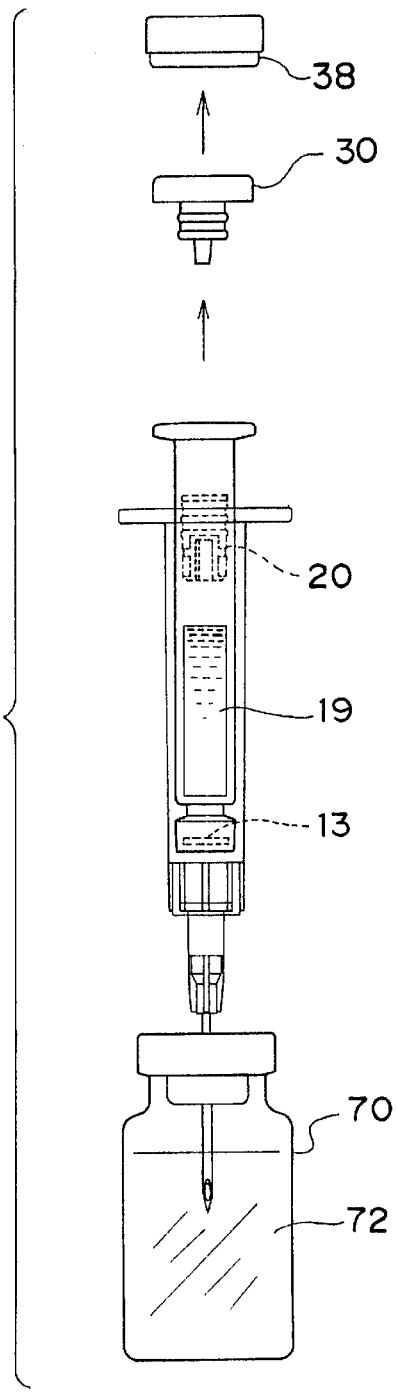

First, as shown in FIG. 17, a needle unit 50 having a needle 52 is attached to a male lure 62 of a holder 60. The holder 60 has an inner needle 64 in its interior. Next, as shown in FIG. 18, the needle 52 is stuck into a vial 70 in which a redissolving solvent 72 is contained, and the tip of the needle 52 is immersed in the redissolving solvent 72. Next, as shown in FIG. 19, the syringe 10 is inserted into the holder 60 from the one end 12a side sealed by the rubber packing 13, and the inner needle 64 of the holder 60 is stuck into the rubber packing 13 so that the vial 70 and the sealed space 12c within the syringe 10 are communicated with each other through the needles 52 and 64. Because the sealed space 12c of the syringe 10 has been reduced in pressure, the redissolving solvent 72 within the vial 70 is sucked into the syringe 10, by which the freeze-dried agent 18 in the syringe 10 is dissolved. Next, as shown in FIG. 20, the flip-off type aluminum cap 38 is removed from the other end 12b side of the syringe 10, the sealing cap 30 is pulled out, and the plunger rod 40 is screwed to the screw hole 28 of the gasket 20. If desired, the redissolving solvent 72 may be further sucked up by pulling the plunger rod 40. In this way, the freeze-dried agent 18 is dissolved with the redissolving solvent 72, thus an injection solution 19 being prepared. Then, as shown in FIG. 21, the needle 52 is pulled out from the vial 70, and as with a normal syringe, with the syringe 10 inserted into the holder 60, the plunger rod 40 is pushed in, by which the injection solution 19 is administered.

As described above, this reduced-pressure syringe 10 is enabled to store the freeze-dried agent 18 under reduced pressure while the sealing cap 30 prevents the gasket 20 plugged under reduced pressure from moving under atmospheric pressure.

It is noted that the present invention may be carried out in other various ways and modes without being limited to the above embodiment. For example, a taper or step may be provided in proximity to the other end 12b of the cartridge 12 so that the sealing cap 30 can be engaged with this taper or step so as to be prevented from moving into the cartridge 12.

What is claimed is:

1. A reduced-pressure syringe comprising:

a generally cylindrical-shaped cartridge having a pair of ends in which one of the ends is openably sealed;

a gasket having a pair of end faces, said gasket slidably provided on a side of the other of the ends of the cartridge, thereby defining a sealed space, where a freeze-dried agent is accommodated in the sealed space, and said gasket having, in its outer circumferential surface, a recessed groove continuing from one of the end faces of the gasket on the side of the one of the ends of the cartridge toward the other of the end faces thereof on the side of the other of the ends thereof to an intermediate position therebetween; and a sealing cap which is to be engaged with an end face of the cartridge on the side of the other of the ends and which seals the side of the other threreof, wherein a pressure in the sealed space is held lower than atmospheric pressure.

2. The reduced-pressure syringe according to claim 1, wherein the gasket has a fitting hole for fitting a plunger rod to the other of the end faces of the gasket on the side of the other of the ends of the cartridge, and the sealing cap has a positioning protrusion which is to be inserted into the fitting hole of the gasket, the positioning protrusion being provided in an end face of the sealing cap on the side of the one (12a) of the ends of the cartridge.

3. A method for manufacturing a reduced-pressure syringe which comprises: a generally cylindrical-shaped cartridge having a pairs of ends in which one of the ends is openably sealed; a gasket having a pair of end faces and having, in its outer circumferential surface, a recessed groove continuing from one of the end faces of the gasket toward the other of the end faces thereof to an intermediate position therebetween; and a sealing cap, the method comprising:

a first step for injecting a specified amount of a chemical into the cartridge with the one of the ends of the cartridge down;

a second step for inserting the gasket halfway on a side of the other of the ends of the cartridge, into which the chemical has been injected, with the recessed groove of the gasket down, so that the cartridge is made communicating between inside and outside through the recessed groove, and then freeze-drying the chemical placed within the cartridge in a freeze-drying chamber under a reduced-pressure atmosphere; and a third step for overlaying the sealing cap on upper one of the end faces of the gasket and pushing the sealing cap toward the cartridge side in the freeze-drying chamber under the reduced-pressure atmosphere so that the side of the other of the ends of the cartridge is sealed by the gasket and the sealing cap, and that the sealing cap is engaged with an end face of the cartridge on the side of the other (12b) of the ends thereof.

* * * * *